(12) United States Patent
Kunelius et al.

(10) Patent No.: US 11,523,731 B2
(45) Date of Patent: Dec. 13, 2022

(54) LARYNGOSCOPE WITH BLADE LOCKING MECHANISM

(71) Applicants: MedSource International LLC, Chanhassen, MN (US); Sikandar Hayat, Sialkot (PK)

(72) Inventors: David Kunelius, Waconia, MN (US); Benjamin Beniek, Richfield, MN (US)

(73) Assignees: MEDSOURCE INTERNATIONAL LLC, Chanhassen, MN (US); Sikandar Hayat, Sialkot (PK)

( * ) Notice: Subject to any disclaimer, the term of this patent is extended or adjusted under 35 U.S.C. 154(b) by 508 days.

(21) Appl. No.: 16/566,005

(22) Filed: Sep. 10, 2019

(65) Prior Publication Data

US 2021/0068627 A1  Mar. 11, 2021

(51) Int. Cl.
*A61B 1/00* (2006.01)
*A61B 1/267* (2006.01)

(52) U.S. Cl.
CPC ...... *A61B 1/00128* (2013.01); *A61B 1/00103* (2013.01); *A61B 1/00124* (2013.01); *A61B 1/267* (2013.01)

(58) Field of Classification Search
CPC ............ A61B 1/00121; A61B 1/00124; A61B 1/00128; A61B 1/00103; A61B 1/00147; A61B 1/267
USPC ........................................................ 600/197
See application file for complete search history.

(56) References Cited

U.S. PATENT DOCUMENTS

2016/0000305 A1\*  1/2016  Elbaz ................. A61B 1/00137
600/193

\* cited by examiner

*Primary Examiner* — Eduardo C Robert
*Assistant Examiner* — Christina Negrellirodriguez
(74) *Attorney, Agent, or Firm* — Westman, Champlin & Koehler, P.A.; Amanda M. Prose

(57) ABSTRACT

A laryngoscope assembly having a handle for connection with a laryngoscope blade and wherein the handle includes an additional mechanism for securing the blade to the handle. A locking mechanism is a spring provided for holding the blade in position on the handle and preventing side to side movement of the blade with respect to the handle.

19 Claims, 4 Drawing Sheets

LARYNGOSCOPE WITH BLADE LOCKING MECHANISM

BACKGROUND

The present invention relates laryngoscopes and more specifically to a laryngoscope configured with a stable blade where side to side movement is prevented during use.

Laryngoscopes are intended to illuminate the larynx or vocal cords for visual inspections. One style of the laryngoscope can be inserted into the patient's mouth to hold down the patient's tongue for a clear view of the patient's throat.

The demand for disposable medical supplies has grown, spurred by the increase in geriatric patients and expanded insurance coverage from the Patient Protection and Affordable Care Act in the U.S. Healthcare organizations have turned to disposables as a response to increased pressure from federal, accreditation organizations and other regulatory bodies to prevent patient and staff harms.

The primary reason for creating disposable devices is infection control. When an item is used only once by a caregiver, it cannot transmit infectious agents to subsequent patients.

While an obvious factor in the design of single-use products could be considered cost, given the nature of medical devices, disposable medical devices require a careful balance between performance, cost, reliability, materials, and shelf life.

Currently, disposable-device assembly depends primarily on injection-molded plastic pieces and/or assembly by bonding, gluing, ultrasonic welding or radio-frequency welding. The high production volume of single-use devices calls for an automated assembly in clean rooms to minimize human contact. Unlike reusable devices, which are often sterilized at the healthcare facility, disposable devices are sterilized before leaving a manufacturing site and are thus provided in a ready-to-use state.

With respect to laryngoscopes, laryngoscope blades are produced in various sizes and the size selected for use depends on the patient's anatomy. Installing disposable blades of different sizes on a laryngoscope handle for use requires a handle that can support both larger and smaller laryngoscope blades. The connection mechanism on the handle then must be configured to accommodate these different sized blades. While the blades in some devices will have a standard hook mechanism for connecting to a bar on the handle, the widths of the blades various and additional movement of the laryngoscope blade cannot be avoided in devices currently on the market. Moreover, when inserting breathing tubes, movement of the blade during the procedure can hinder placement of the tube, resulting in patient injury.

SUMMARY

An aspect of the present disclosure relates to a laryngoscope having a handle for removable connection with a disposable laryngoscope blade. The handle is a housing having a first mechanism for operably securing the laryngoscope blade to the handle. The handle further comprises a second mechanism for retaining the laryngoscope blade in a selected position when the laryngoscope blade is connected to the first mechanism.

In one or more embodiments, the first mechanism is a crossbar extending across an end portion of the handle and is configured for receiving a hooked portion of the laryngoscope blade to secure the laryngoscope blade to the handle. The second mechanism is a locking mechanism configured to prevent side to side movement of the laryngoscope blade connected to the handle.

In one or more embodiments, the second mechanism is a spring supported by the housing and configured for locking the laryngoscope blade in a selected position on a length of the crossbar by providing a stabilizing force between the housing and the laryngoscope blade for eliminating side to side movement of the laryngoscope blade along the crossbar between sides of the housing.

The handle has a head portion comprising two opposing side arms spaced laterally apart and extending upwardly from the housing and where the first mechanism extends between a connection with each of the side arms and wherein the second mechanism is positioned on a vertical surface of one of the opposing side arms.

Another aspect of the present disclosure relates to a handle for operably supporting various laryngoscope blades of the same or different size or style. The handle has a base and a head with a length extending therebetween wherein the head supports a crossbar for operably connecting a selected laryngoscope blade to the handle and a locking mechanism for engaging with the laryngoscope blade to prevent or eliminate side to side movement of the laryngoscope blade connected to the crossbar during use.

The head comprises two opposing side arms spaced laterally apart and extending upwardly from a connection with the handle and the crossbar extends between these side arms and the locking mechanism is positioned on one of the opposing side arms.

In one or more embodiments the locking mechanism comprises a spring. The spring is positioned on an inner facing surface of one opposing side arm for stabilizing the blade with respect to side to side movement along the crossbar. The spring frictionally engages with the laryngoscope blade to prevent side to side movement of the blade along the crossbar.

The base supports a battery therein for powering a light source and the base further comprises a cap for access to the battery.

The head supports a mechanism for mechanically engaging the handle with the blade and electrically engaging the battery supported by the handle with a light source positioned on the blade.

Yet another aspect of the present disclosure relates to a method of using a laryngoscope. The method comprises providing a handle having a base portion and a head portion with a length extending therebetween wherein the head portion supports an attachment mechanism for operably supporting a selected laryngoscope blade and a locking mechanism for engaging with the supported laryngoscope blade. The method further comprises connecting the selected laryngoscope blade to the attachment mechanism and engaging the selected laryngoscope blade with the locking mechanism to secure the blade as connected to the attachment mechanism.

The attachment mechanism is a crossbar extending between two opposing spaced apart side arms of the head portion and connecting the selected laryngoscope blade to the attachment mechanism comprises hooking an end of the laryngoscope blade to the crossbar.

The locking mechanism comprises a spring positioned in an interior centered area of the head portion and supported by at least one of the spaced apart side arms of the head portion such that the spring provides frictional engagement with the selected laryngoscope blade to hold the selected laryngoscope blade in a position on the attachment mechanism thus stabilizing the laryngoscope blade for use The laryngoscope blade is further engaged in electrical connection with the handle for providing battery power from the handle to a light source positioned on the laryngoscope blade.

DETAILED DESCRIPTION

Figure 1:
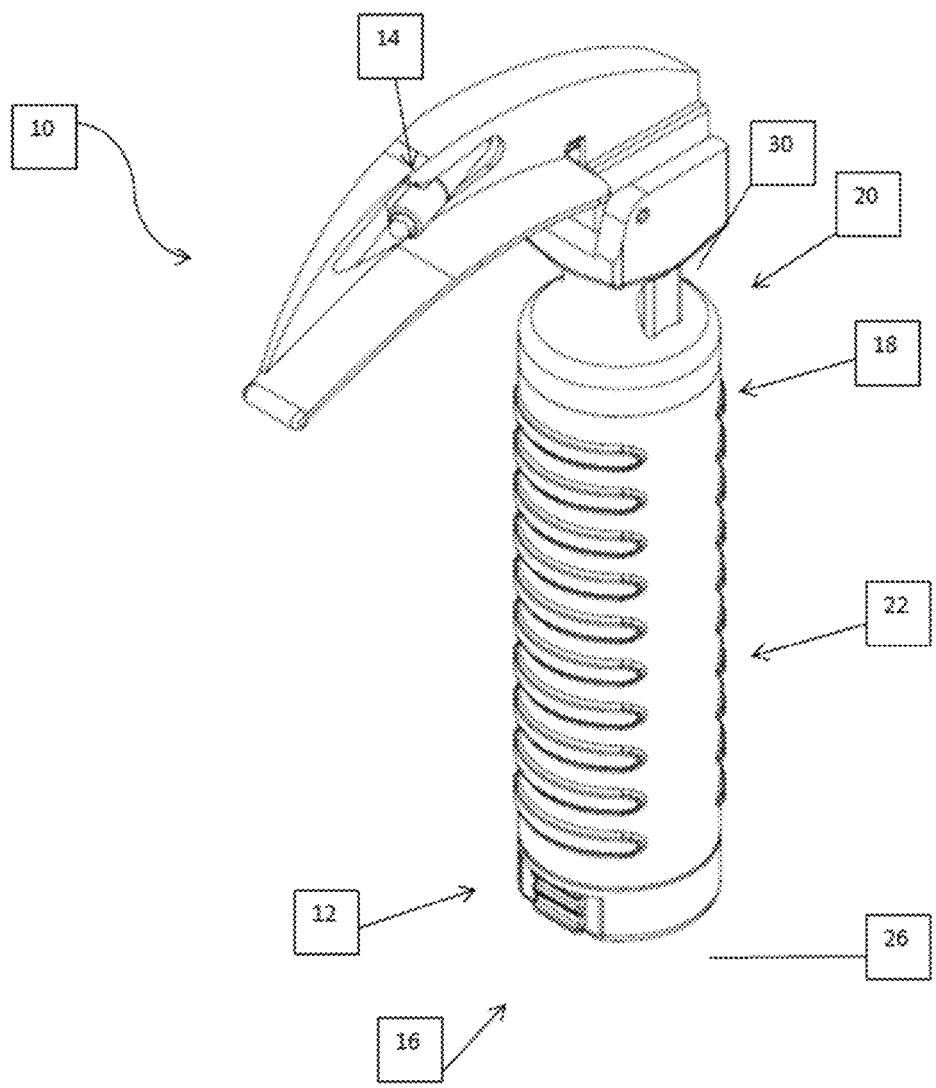
FIG. 1 is a back perspective view of a laryngoscope according to the present disclosure.

A laryngoscope 10 is illustrated in FIGS. 1-4. The Laryngoscope 10 when assembled comprises a handle 12 and a blade 14. The handle 12 may be used with various sized blades 14 wherein the blades 14 are single-use, disposable blades 14. The handle 12 has a first end 16 and a second opposing end 18 which terminates in a handle head portion 20 which is configured for operable connection with the blade 14. A gripping or use length 22 extends between the first and second ends of the handle 10. In operation, a user holds the laryngoscope 10 at or around the handle 12.

The laryngoscope 10 described herein includes a laryngoscope where the blade 14 is a single-use, disposable blade 14 and wherein the handle 12 may also be a disposable handle. The handle 12 and blade 14 may be provided together or separately as individual components and further the handle 12 and blade 14 may be provided in either an assembled or disassembled state. Various blade 14 sizes and styles may be provided with the same handle 12 or only one blade 14 size may be provided with the handle 12. Any one or more blade size or style may be provided with the same or substantially similar handle construction, configuration and/or dimensions.

The handle 12 may also be referred to herein as a housing 12. The housing can support electrical components such as a battery and corresponding wiring for powering a light source 24 of the laryngoscope 10. A cap 26 such as a pinch cap may be provided at the first end 16 or base 16 of the handle 12 for easy battery access and disposal.

The light source 24 may be positioned on the blade 14 for illumination into the mouth or throat of the patient when the laryngoscope 10 is in use. Examples of light sources 24 include but are not limited LED light sources or other cold light sources. LED laryngoscopes are considered cold light. In cold light the body of the laryngoscope does not heat up when the light source is on as there is insufficient heat generated to raise the temperature of the scope itself.

Figure 2:
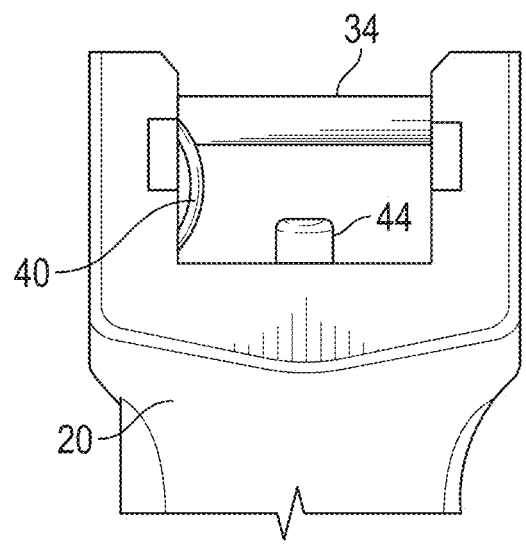
FIG. 2 is a front view of a head portion of a handle of the laryngoscope.
Figure 3:
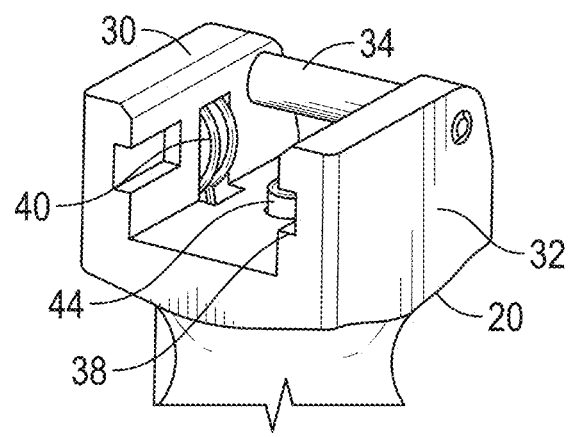
FIG. 3 is a perspective view of the head portion of the handle of the laryngoscope.

Referring to FIGS. 2-3, the head portion 20 of the handle 12 comprises opposing side arms 30 and 32 which may be integrally formed with and extend upwardly from the length 22 of the handle 12. The head portion 20 is configured for supporting various sized laryngoscope blades 14. The side arms 30 and 32 are spaced apart according to the dimensions of the handle 12 such that there is an open space between the side arms 30 and 32 for the connection with the blade 14. A floor 28 separates the arms 30 and 32 at the body or length of the handle 12.

In further detail, the head portion 20 of the handle 12 supports a crossbar 34 which extends across the head portion 20 from connection with each opposing side arm 30 and 32. A first end or connecting end 36 of the blade 14 is secured to the crossbar 30. For example, the blade 14 may have a hooked end 36 for hooked connection to or about the crossbar 34 to secure the blade 14 to the crossbar 34 for use. Once connected to the crossbar 34, the blade 14 is stable with respect to pivotal movement such as forward or backward movement on the handle 12. However, as the blade 14 is selected depending on the end use and patient anatomy and as the handle 12 is configured to support various size laryngoscope blades 14, the space between the arms 30 and 32 may be greater than a width of the blade 14.

Figure 4:
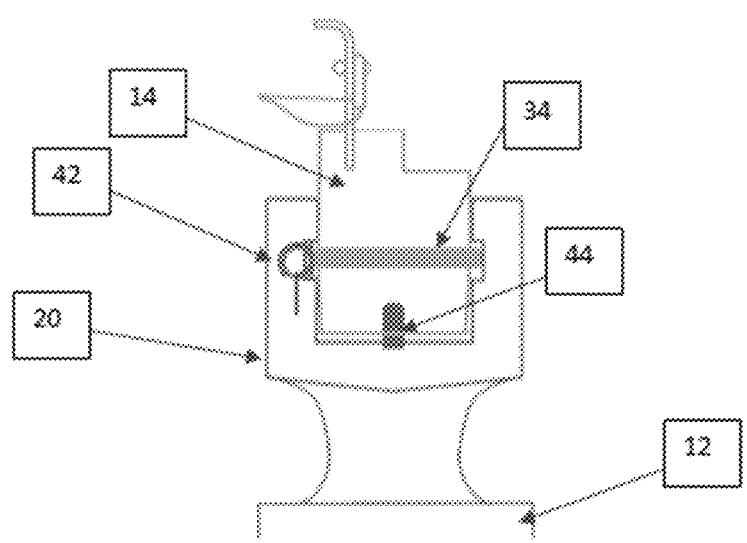
FIG. 4 is a front cross-sectional view of the head of the laryngoscope with a blade engaged with the head.
Figure 5:
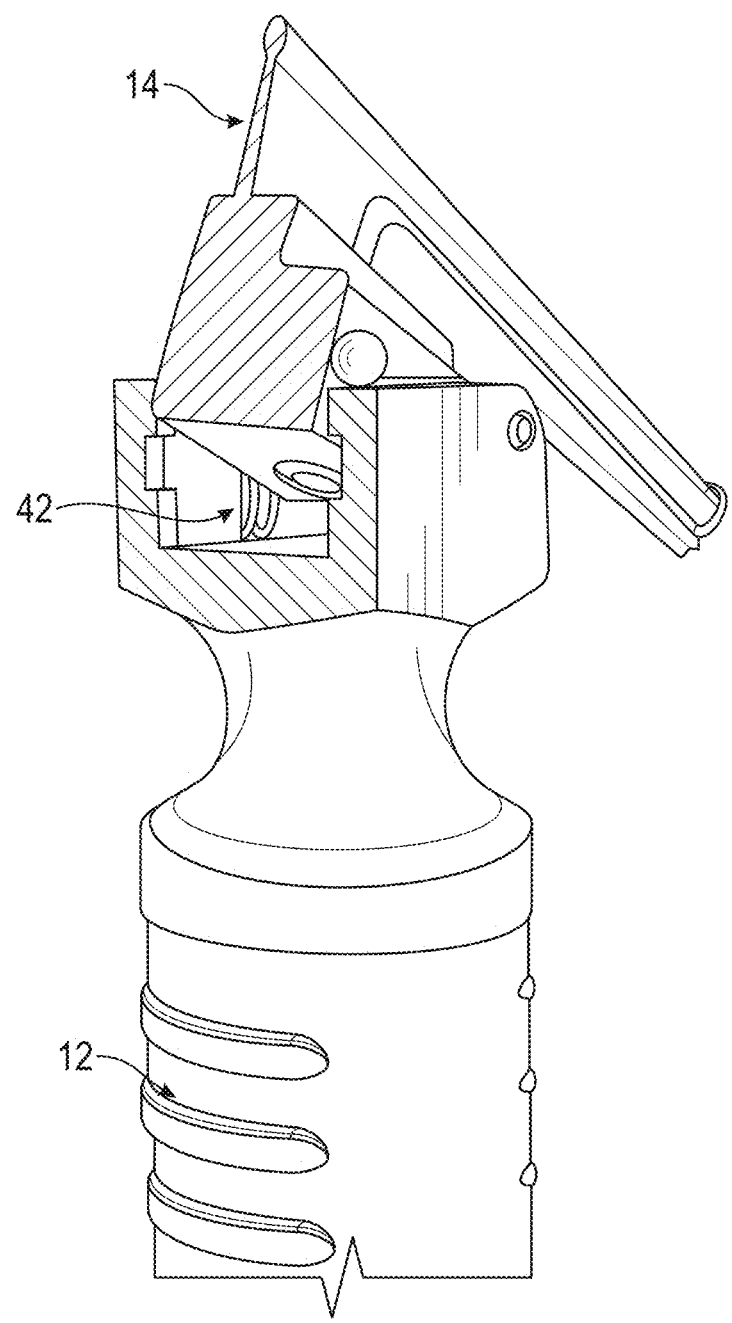
FIG. 5 is a front perspective view of the laryngoscope.

A locking mechanism 40 is provided to prevent side to side movement of the blade 14 connected to the handle 12, regardless of the side or style of the blade 14. The locking mechanism effectively eliminates the side to side movement of the blade 14 along the crossbar 34 to stably and securely hold the blade 14 in place for safer and easier use of the laryngoscope 10 as illustrated in FIG. 4.

In one embodiment, the locking mechanism 40 is positioned along or is otherwise supported by one side arm 30 or 32, however other arrangements and positioning for the locking mechanism 40 are contemplated and within the scope of this disclosure. In the embodiment illustrated, the locking mechanism 40 comprises a spring 42. The spring 42 is positioned to provide frictional engagement between the head portion 20 and the blade 14 to prevent side to side movement of the blade and to further secure the blade 14 to the handle 12. The locking mechanism 40 is the stability locking spring 42 that is more specifically located on an interior center of the head portion 20. Thus, the spring 42 extends into the space between the opposing arms 30 and 32 and frictionally engages with a blade 14 to prevent the blade from sliding on the crossbar 34.

The floor 38 of the head portion 20 extends between a base of each arm 30 and 32 and supports a lamp base 44. The lamp base 44 may be a metallic outer housing of a lamp which provides electrical contact for connecting the power source supported by the handle 12 to the light source 24 positioned on the blade 14. The lamp base 44 also provides a mechanical engagement between the head portion 20 and the blade 14 when the blade is installed. Mechanical attachment of the blade 14 to the handle 12 ensures that the blade 14 remains coupled to the handle 12 in all positions of the blade 14.

The blades 14 may come in a variety of sizes and styles depending on end use. The patient's anatomy also dictates the size of the blade 14 that will be used with the handle 12 and the style of blade 14 may also be selected based on the end use of the assembled laryngoscope 10. Generally, laryngoscope blades are provided in two models, Macintosh Blades or Miller Blades, including the shape of the blade. The blades have an end configured for engagement with the handle, and the engagement mechanism may vary but generally the blade hooks to a mating component on the handle. The opposing end of the blade is configured for insertion into a patient's mouth to access the throat.

The disposable blades 14 may be stainless steel blades that are sterilized and packaged ready for use in a medical setting. The blades 14 may alternatively be comprised of other suitable materials including but not limited to high impact grate ABS plastic materials.

One or both of the blade 14 and the handle 12 may be disposable elements configured for single use. A single-use, disposable blade 14 of a range of blade sizes can be operably and stably connected to the base 12 and secured in place via the locking mechanism 40 which engages with the blade 14 substantially regardless of blade size. A smaller handle 12 may be provided with reduced dimensions on a pediatric scale such that the handle 12 and blades 14 are substantially the same in component arrangement but are smaller for use with children. In both embodiments, a selected laryngoscope blade will be further secured in place via frictional engagement with the locking mechanism 40.

The laryngoscope described herein is further configured for disengaging the selected laryngoscope blade from the locking mechanism and attachment mechanism after a single use and discarding the laryngoscope blade. A second or subsequent blade may then be connected to the attachment mechanism and engaged with the locking mechanism to secure the blade as connected to the attachment mechanism of a first handle or a subsequent second handle.

Although the present disclosure has been described with reference to preferred embodiments, workers skilled in the art will recognize that changes may be made in form and detail without departing from the spirit and scope of the disclosure.

The invention claimed is:

1. A handle for operably supporting a laryngoscope blade, the handle comprising: a base and a head with a length extending therebetween, wherein the head comprises a crossbar for operably supporting the laryngoscope blade, and a locking mechanism comprising a spring located on an interior center of the head and protruding into a space on the head for receiving and engaging with the laryngoscope blade installed thereon to prevent or eliminate side to side movement of the laryngoscope blade supported on the crossbar during use.

2. The handle of claim 1 wherein the head comprises two opposing side arms spaced laterally apart and extending upwardly from a connection with a length extending therefrom where the crossbar extends between the side arms and wherein the spring is positioned on one of the opposing side arms.

3. The handle of claim 2 wherein the wherein the spring is oriented with a coil length extended between opposing ends of the spring in a direction transverse to the direction of the crossbar.

4. The handle of claim 3 wherein the spring is positioned on an inner facing surface of one opposing side arm for stabilizing the blade with respect to side to side movement along the crossbar.

5. The handle of claim 3 wherein the handle is configured for supporting disposable blades of different sizes.

6. The handle of claim 2 wherein the base supports a battery for powering a light source and the base further comprises a cap for access to the battery.

7. The handle of claim 2 wherein the head further comprises a mechanism for mechanically engaging the handle with the blade and electrically engaging a battery supported by the handle with a light source positioned on the blade.

8. A laryngoscope having a handle for connection with a disposable laryngoscope blade, wherein the handle is a housing comprising: a first mechanism for operable connection with the laryngoscope blade and wherein the first mechanism secures the laryngoscope blade to the handle, and a second mechanism for retaining the laryngoscope blade in a selected position when the laryngoscope blade is connected to the first mechanism, wherein the second mechanism is a spring biased locking mechanism with a spring supported on the housing and a length of the spring being parallel to a length of the laryngoscope blade installed on the handle.

9. The laryngoscope of claim 8 wherein the first mechanism is a crossbar extending across an end portion of the handle and configured for receiving a hooked portion of the laryngoscope blade to secure the laryngoscope blade to the handle.

10. The laryngoscope of claim 8 wherein the spring supported on the housing is configured for locking the laryngoscope blade in a selected position on a length of the crossbar by eliminating side to side movement of the laryngoscope blade along the crossbar between sides of the housing.

11. The laryngoscope of claim 8 wherein the handle has a head portion comprising two opposing side arms spaced laterally apart and extending upwardly from the housing and where the first mechanism extends between a connection with each of the side arms, and wherein the second mechanism is positioned on a vertical surface of one of the opposing side arms.

12. The laryngoscope of claim 11 wherein the first mechanism is a crossbar for connecting to the laryngoscope blade and the second mechanism is a spring locking mechanism for preventing side to side movement of the laryngoscope blade on the crossbar.

13. A method of using a laryngoscope comprising:
providing a handle having a base portion and a head portion with a length extending therebetween wherein, the head portion supports an attachment mechanism for operably supporting a selected laryngoscope blade, and a spring for engaging with the supported laryngoscope blade installed thereon;
connecting the selected laryngoscope blade to the attachment mechanism;
engaging the selected laryngoscope blade with a side length of the spring of the locking mechanism to secure the blade as connected to the attachment mechanism.

14. The method of claim 13 wherein the attachment mechanism is a crossbar extending between two opposing spaced apart side arms of the head portion, and connecting the selected laryngoscope blade to the attachment mechanism comprises hooking an end of the laryngoscope blade to the crossbar.

15. The method of claim 14 wherein the locking mechanism comprises the spring positioned in an interior centered area of the head portion and supported by at least one of the two opposing spaced apart side arms of the head portion such that the spring provides frictional engagement with the selected laryngoscope blade to hold the selected laryngoscope blade in a position on the attachment mechanism thus stabilizing the laryngoscope blade for use.

16. The method of claim 15 and further engaging the laryngoscope blade in electrical connection with the handle for providing battery power from the handle to a light source positioned on the laryngoscope blade.

17. The method of claim 15 and further comprising:
disengaging the laryngoscope blade from the locking mechanism and attachment mechanism after a single use;
discarding the laryngoscope blade; and
connecting a subsequent selected laryngoscope blade to the attachment mechanism;
engaging the subsequent selected laryngoscope blade with the locking mechanism to secure the blade as connected to the attachment mechanism.

18. The method of claim 17 wherein the selected laryngoscope blade and the subsequent selected laryngoscope blade are different in size or style.

19. The method of claim 18 wherein the locking mechanism spring engages the subsequent selected laryngoscope blade to hold the subsequent selected laryngoscope blade in a position on the attachment mechanism thus stabilizing the subsequent laryngoscope blade for use.

\* \* \* \* \*